(12) United States Patent
Wahrenberg

(10) Patent No.: US 12,210,094 B2
(45) Date of Patent: Jan. 28, 2025

(54) RENDERING METHOD AND APPARATUS

(71) Applicant: CANON MEDICAL SYSTEMS CORPORATION, Otawara (JP)

(72) Inventor: Magnus Wahrenberg, Edinburgh (GB)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 64 days.

(21) Appl. No.: 17/880,722

(22) Filed: Aug. 4, 2022

(65) Prior Publication Data
US 2024/0045057 A1    Feb. 8, 2024

(51) Int. Cl.
*A61B 8/06* (2006.01)
*A61B 8/08* (2006.01)
(Continued)

(52) U.S. Cl.
CPC .......... *G01S 15/8988* (2013.01); *A61B 8/06* (2013.01); *A61B 8/488* (2013.01);
(Continued)

(58) Field of Classification Search
CPC .......... G01S 15/8988; G01S 7/52071; G01S 15/8993; A61B 8/06; A61B 8/488;
(Continued)

(56) References Cited

U.S. PATENT DOCUMENTS 5,840,032 A * 11/1998 Hatfield ............. G01S 7/52085
                                                      348/E13.064
6,102,864 A *  8/2000 Hatfield ............... G06T 7/0012
                                                      600/454
(Continued)

FOREIGN PATENT DOCUMENTS

CN    112598619 A    4/2021
CN    113876352 A    1/2022
(Continued)

OTHER PUBLICATIONS

Fenster et al., "Three-dimensional ultrasound imaging", Physics in Medicine and Biology, 46(5), 2001, pp. R67-99. doi: 10.1088/0031-9155/46/5/201. PMID: 11384074.
(Continued)

*Primary Examiner* — Abderrahim Merouan
(74) *Attorney, Agent, or Firm* — Oblon, McClelland, Maier & Neustadt, L.L.P.

(57) ABSTRACT

A medical imaging apparatus comprises processing circuitry configured to: receive three-dimensional flow data, wherein the three-dimensional flow data comprises data acquired by medical imaging of a subject; perform a first intensity projection to process first flow data corresponding to a first region in the three-dimensional flow data having a first direction of flow, thereby obtaining a first color; perform a second, independent intensity projection to process second flow data corresponding to a second region in the three-dimensional flow data having a second direction of flow which is different from the first direction of flow, thereby obtaining a second color; combine the first color and the second color to obtain a combined color; and generate volume rendering image data based on the combined color.

20 Claims, 4 Drawing Sheets

(51) Int. Cl.
   *G01S 7/52* (2006.01)
   *G01S 15/89* (2006.01)
   *G06T 7/00* (2017.01)
   *G06T 15/04* (2011.01)
   *G06T 15/08* (2011.01)

(52) U.S. Cl.
   CPC ...... *G01S 7/52071* (2013.01); *G01S 15/8993* (2013.01); *G06T 7/0012* (2013.01); *G06T 15/04* (2013.01); *G06T 15/08* (2013.01); *G06T 2200/04* (2013.01); *G06T 2207/10024* (2013.01); *G06T 2207/10081* (2013.01); *G06T 2207/10088* (2013.01); *G06T 2207/10136* (2013.01); *G06T 2207/30104* (2013.01); *G06T 2210/41* (2013.01)

(58) Field of Classification Search
   CPC ....... G06T 7/0012; G06T 15/04; G06T 15/08; G06T 2207/10081; G06T 2207/10088; G06T 2207/10136; G06T 2207/30104; G06T 2210/41
   See application file for complete search history.

(56) References Cited

U.S. PATENT DOCUMENTS

| | | | | |
|---|---|---|---|---|
| 6,664,961 | B2* | 12/2003 | Ray | H04N 13/275 348/E13.057 |
| 10,702,231 | B2* | 7/2020 | Ohishi | A61B 6/504 |
| 2007/0167773 | A1 | 7/2007 | Jeong et al. | |
| 2015/0018684 | A1 | 1/2015 | Abe et al. | |
| 2015/0045666 | A1* | 2/2015 | Lin | A61B 8/5223 600/441 |
| 2015/0097833 | A1 | 4/2015 | Razeto et al. | |
| 2017/0119356 | A1* | 5/2017 | Steininger | A61B 8/488 |
| 2018/0279970 | A1* | 10/2018 | Ohishi | A61B 6/507 |
| 2018/0344261 | A1* | 12/2018 | Yoshida | A61B 5/055 |
| 2019/0244352 | A1* | 8/2019 | Honjo | G06T 7/11 |
| 2019/0320875 | A1* | 10/2019 | Jones | G06T 7/0012 |
| 2019/0357874 | A1 | 11/2019 | Yoshiara et al. | |
| 2020/0193689 | A1 | 6/2020 | Kato et al. | |
| 2020/0198294 | A1* | 6/2020 | Lee | B32B 7/023 |
| 2021/0043140 | A1* | 2/2021 | Roh | G09G 3/3258 |
| 2021/0049734 | A1 | 2/2021 | Wahrenberg et al. | |
| 2021/0100522 | A1 | 4/2021 | Nickisch et al. | |
| 2021/0128100 | A1* | 5/2021 | Honjo | G01S 7/52063 |
| 2021/0192685 | A1* | 6/2021 | Nomura | H04N 23/843 |
| 2022/0076502 | A1* | 3/2022 | Hu | G06T 15/04 |
| 2022/0179205 | A1* | 6/2022 | Marcotte | G06N 20/00 |
| 2023/0011603 | A1* | 1/2023 | Choi | H04M 1/0283 |
| 2023/0095507 | A1* | 3/2023 | Kim | C09D 11/037 257/98 |
| 2023/0225642 | A1* | 7/2023 | Margiott | A61B 5/14551 |
| 2023/0290088 | A1* | 9/2023 | Eble | G06T 19/006 |

FOREIGN PATENT DOCUMENTS

| | | |
|---|---|---|
| EP | 3 928 294 A1 | 12/2021 |
| JP | 2002-191600 A | 7/2002 |
| JP | 2013-121453 A | 6/2013 |
| WO | WO 2011/099410 A1 | 8/2011 |
| WO | WO 2014/168249 A1 | 10/2014 |
| WO | WO 2021/187675 A1 | 9/2021 |

OTHER PUBLICATIONS

Oglat et al., "A Review of Medical Doppler Ultrasonography of Blood Flow in General and Especially in Common Carotid Artery", Journal of Medical Ultrasound, 26(1), 2018, pp. 3-13. doi: 10.4103/JMU.JMU_11_17.

* cited by examiner

RENDERING METHOD AND APPARATUS

FIELD

Embodiments described herein relate generally to an apparatus and method for volume rendering, for example a method for rendering an image from ultrasound color Doppler imaging data.

BACKGROUND

Ultrasound color Doppler imaging is known. Ultrasound can be used to acquire information on flow of bodily fluids on a voxel-by-voxel basis by measuring Doppler shift for each of a plurality of voxels in an image volume.

Ultrasound color Doppler imaging may be performed with two-dimensional or three-dimensional data, which may be live data.

A signal obtained in ultrasound color Doppler imaging generally includes a power component (which may also be referred to as a strength component), a velocity component, and a turbulence component (which may also be referred to as a variance component).

Consider an ultrasound imaging scenario in which a transducer transmits ultrasound having a frequency f into a region of tissue comprising blood flowing in a vessel. A Doppler frequency may be written as $f_d=2f_t V \cos \theta /c$, where $f_d$ is the Doppler shift, c is the speed of sound in tissue, $f_t$ is a frequency of a transmitted ultrasound beam, V is a flow velocity of blood being imaged, and θ is an angle of incidence between the ultrasound beam and the direction of the flow of blood. A higher Doppler frequency is obtained as the velocity is increased, the transmitted beam is more aligned to the flow direction and/or a higher frequency is used.

Two-dimensional ultrasound color Doppler data may be easily visualized using a simple color mapping. Three-dimensional ultrasound color Doppler acquisitions may be more complicated and difficult to represent as an image.

Flow may generally be a very complicated signal. Larger regions of flow, for example heart chambers, may have both forward and backward flow within the same region, for example within the same heart chamber. A vessel will typically have slower flow towards the edges of the vessel than in the center of the vessel, even under laminar flow conditions.

Volume rendering of ultrasound color Doppler data may generally show structures well, but the flow signal shown in rendered images may be mainly a flow signal boundary of the flow. For example, in a volume rendered vessel tree, what is shown may be mainly the outside of the vessels.

It is possible to use maximum intensity projection (MIP) rendering to visualize ultrasound color Doppler data. MIP rendering is mainly used on the power signal or the velocity magnitude. Using MIP rendering on the power signal or the velocity magnitude fails to visualize directionality, which is an important part of the signal. A complex region having both forward and backward flow may be shown as a single bright region which does not distinguish direction. Vessels may only retain their shape.

SUMMARY

In a first aspect, there is provided a medical imaging apparatus comprising processing circuitry configured to: receive three-dimensional flow data, wherein the three-dimensional flow data comprises data acquired by medical imaging of a subject; perform a first intensity projection to process first flow data corresponding to a first region in the three-dimensional flow data having a first direction of flow, thereby obtaining a first color; perform a second, independent intensity projection to process second flow data corresponding to a second region in the three-dimensional flow data having a second direction of flow which is different from the first direction of flow, thereby obtaining a second color; combine the first color and the second color to obtain a combined color; and generate volume rendering image data based on the combined color.

The medical imaging may comprise ultrasound Doppler imaging. The medical imaging may comprise ultrasound color Doppler imaging. The medical imaging may comprise MRI FBI (Fresh Blood Imaging). The medical imaging may comprise FFR-CT (fractional flow reserve CT) imaging.

The three-dimensional flow data may comprise three-dimensional blood flow data. The three-dimensional flow data may be representative of a flow of urine. The three-dimensional flow data may be representative of a flow of cerebrospinal fluid.

The three-dimensional flow data may comprise at least a respective power value and a respective velocity value for each of a plurality of voxels.

The processing circuitry may be configured to determine whether voxels of the three-dimensional flow data are part of the first region or second region based on the velocity values.

The processing circuitry may be configured to apply a power threshold to voxels of the three-dimensional flow data. The applying of the power threshold may be such that the first intensity projection and second intensity projection process voxels having a power value above the power threshold.

The first direction of flow may be forward. The second direction of flow may be backward.

The first direction of flow may be forward relative to a direction of acquisition, for example relative to a position of an ultrasound transducer probe. The second direction of flow may be backward relative to the direction of acquisition, for example relative to a position of the ultrasound transducer probe. The first direction of flow may be forward relative to a vessel or other anatomical structure of the subject. The second direction of flow may be backward relative to the vessel or other anatomical structure.

The performing of the first intensity projection may comprise accumulating velocity values for the first region over at least part of a ray that traverses a volume of the three-dimensional flow data. The performing of the second intensity projection may comprise accumulating velocity values for the second region over the at least part of the ray. The accumulating of the velocity values for the first and second region may be performed until an accumulation condition is reached.

The accumulation condition may comprise the ray exiting the volume. The accumulation condition may comprise a predetermined number of samples falling below a or the power threshold. The accumulation condition may comprise an accumulation of difference in power values falling under a cumulative power threshold.

The processing circuitry may be further configured to perform further first and second intensity projections along a further part of the ray to obtain further first and second colors. The processing circuitry may be further configured to combine the further first and second colors to obtain a further combined color. The processing circuitry may be further configured to composite the combined color and the further combined color.

The compositing of the combined color and the further combined color may maintain an order along the ray.

The obtaining of the first color may comprise obtaining the first color from a first color mapping resource. The obtaining of the second color may comprise obtaining the second color from a second, different color mapping resource. The first color mapping resource may comprise a first lookup table. The second color mapping resource may comprise a second, different lookup table.

The combining of the first color and the second color may be performed using a combining operator.

The combining operator may combine the first color and second color such that the first color for the forward direction is over the second color for the backward direction. The combining operator may combine the first color and second color such that the second color for the backward direction is over the first color for the forward direction.

The processing circuitry may be configured to determine which of the first flow data and the second flow data has the faster flow. The combining operator may combine the first color and second color such that the one of the first color and second color that corresponds to the flow data having the faster flow is over the other of the first color and the second color.

The processing circuitry may be configured to determine which of the first flow data and the second flow data has the higher power. The combining operator may combine the first color and second color such that the one of the first color and second color that corresponds to the flow data having the higher power is over the other of the first color and the second color.

The processing circuitry may be configured to determine which of the first flow data and the second flow data has the most samples over a or the power threshold. The combining operator may combine the first color and second color such that the one of the first color and second color that corresponds to the flow data having the most samples over said power threshold is over the other of the first color and the second color.

The combining operator may add the first color and the second color.

The processing circuitry may determine a maximum power of the first flow data. The processing circuitry may determine a maximum power of the second flow data. The combining operator may modulate the first color using the maximum power of the first flow data. The combining operator may modulate the second color using the maximum power of the second flow data. The combining operator may add the modulated first color and the modulated second color.

The method may further comprise performing a further volume rendering of the three-dimensional flow data to obtain further volume rendering image data, and combining or overlaying the volume rendering image data with the further volume rendering image data.

In a further aspect, which may be provided independently, there is provided a medical imaging method comprising: receiving three-dimensional flow data, wherein the three-dimensional blood flow data comprises data acquired by medical imaging of a subject; performing a first intensity projection to process first flow data corresponding to a first region in the three-dimensional flow data having a first direction of flow, thereby obtaining a first color; performing a second, independent intensity projection to process second flow data corresponding to a second region in the three-dimensional flow data having a second direction of flow which is different from the first direction of flow, thereby obtaining a second color; combining the first color and the second color to obtain a combined color; and generating volume rendering image data based on the combined color.

In a further aspect, which may be provided independently, there is provided a medical imaging apparatus comprising processing circuitry configured to acquire a three-dimensional blood flow data by ultrasound doppler imaging for a subject; MIP (Minimum Intensity Projection) process a first blood data corresponding to a first region in the three-dimensional blood flow data based on the projection direction of each ray and a second blood data corresponding to a second region in the three-dimensional blood flow data independently; combine the MIP processed first blood data and the second blood data; and generate the volume rendering image data based on the combined data.

In a further aspect, which may be provided independently, there is provided a medical imaging method comprising a color Doppler volume comprising at least a power and directional velocity signal; an intensity projection mode; a forwards and a backwards color table, or velocity to color mapping method; an intensity projection mode; a color combining operator; and a projected ray traversal stepping through the volume; in which in which each voxel above a power threshold is classified as forward or backward flow and the velocity accumulated separately using the intensity projection mode until the composition condition is reached. The two accumulated velocity values are passed through the color table/mapping method and combined using the operator and composited/written to the pixel value.

The composition condition may be the ray exiting the volume.

The composition condition may be the sample falling below the power threshold having previously been above the threshold.

A set of N samples below the power threshold may be required to trigger the composition condition.

An accumulation of difference in power values below the power threshold falling under a cumulative power threshold may triggers the composition condition.

The combining operator may be at least one of: based on compositing; static forward direction over backward and vice-versa; fastest flow on top; highest power on top; main component on top, where the main component is the direction having the most valid (above power threshold) samples during the accumulation; additive; clamped forward and backwards color; power modulated; Max forward power*forward color+Max backwards power*backwards color/(Max forward power+max backwards power).

In a further aspect, which may be provided independently, there is provided a medical imaging apparatus comprising processing circuitry configured to: acquire three-dimensional blood flow data by ultrasound doppler imaging for a subject, perform an intensity projection process based on the projection of ray(s) in respect of first blood data corresponding to a first region in the three-dimensional blood flow data, and in respect of second blood data corresponding to a second region in the three-dimensional blood flow data independently, combine the processed first blood data and processed second blood data, generate the volume rendering image data based on the combined data.

The first region may comprises a set of voxels for which there is forward flow. The second region may comprise a set of voxels for which there is backward flow.

The blood flow data may comprise at least a power and velocity signal. The intensity projection method may comprise a projected ray traversal stepping through a volume, in which in which each voxel above a power threshold is classified as forward flow or backward flow and velocity values are accumulated separately for forward flow and backward flow using the intensity projection until a composition condition is reached. The combining and generating may comprise passing the two accumulated velocity values, corresponding to forward flow and backward flow, through a forward color table or backward color table, or to a velocity to color mapping method and then combining them using a color combining operator to obtain a corresponding pixel value.

The composition condition may comprise the ray exiting the volume. The composition condition may comprise a sample value falling below the power threshold having previously been above the threshold. A set of N samples below the power threshold may be required to trigger the composition condition, where N is an integer >1. The composition condition may comprise a comparison of a cumulative power threshold to an accumulation of difference in power values below the threshold.

Features in one aspect may be provided as features in any other aspect as appropriate. For example, features of a method may be provided as features of an apparatus and vice versa. Any feature or features in one aspect may be provided in combination with any suitable feature or features in any other aspect.

BRIEF DESCRIPTION OF THE DRAWINGS

Embodiments are now described, by way of non-limiting example, and are illustrated in the following figures, in which.

DETAILED DESCRIPTION

Figure 1:
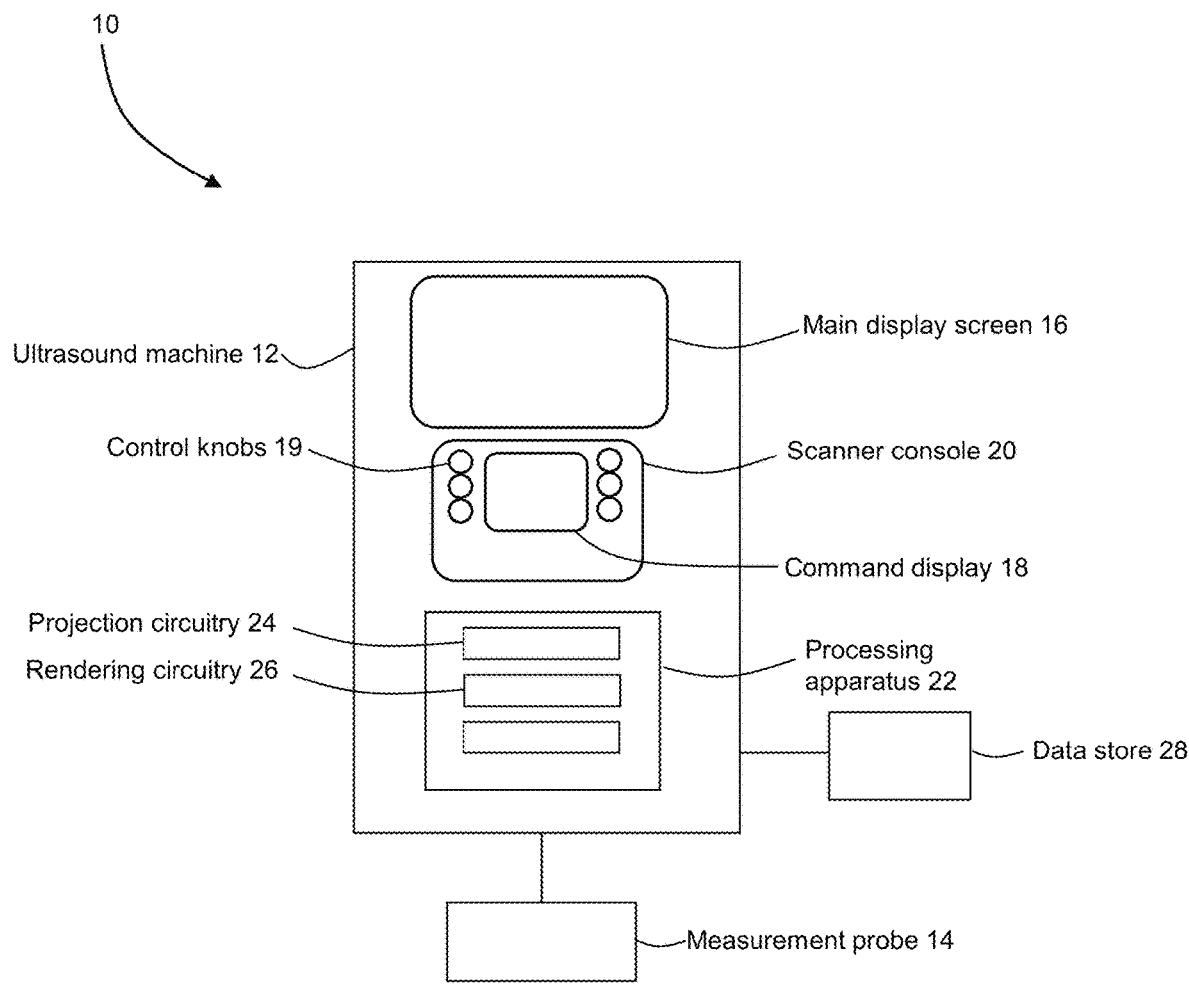
FIG. 1 is a schematic illustration of an apparatus in accordance with an embodiment.

An apparatus 10 according to an embodiment is illustrated schematically in FIG. 1. The apparatus 10 is configured to acquire ultrasound data from an ultrasound scan and to process the ultrasound data to obtain an ultrasound image.

The apparatus 10 comprises an ultrasound machine 12 and associated measurement probe 14. Any suitable type of ultrasound machine 12 and measurement probe 14 may be used. In other embodiments the medical diagnostic apparatus 10 may comprise or be in communication with a scanner apparatus of an alternative modality, for example, a magnetic resonance (MR or MRI) scanner, CT (computed tomography) scanner, cone-beam CT scanner, X-ray scanner, PET (positron emission tomography) scanner or SPECT (single photon emission computed tomography) scanner.

The ultrasound machine 12 comprises a main display screen 16 for displaying a main ultrasound image. The ultrasound machine 12 further comprises a scanner console 20. The scanner console 20 comprises a control screen 18 for displaying control information and input devices comprising various control knobs 19. The input devices may further comprise a computer keyboard, a mouse or a trackball (not shown). In the present embodiment, the control screen 18 is a touch screen, which is both a display device and a user input device. Further embodiments may comprise a control screen 18, display screen or main display screen 16 that does not form part of the ultrasound machine 12. The ultrasound machine 12 also comprises a data store 28.

The ultrasound machine 12 comprises a processing apparatus 22 for processing of data, including image data. The processing apparatus 22 comprises a Central Processing Unit (CPU) and Graphical Processing Unit (GPU). The processing apparatus 22 includes projection circuitry 24 and rendering circuitry 26. The projection circuitry 24 and rendering circuitry 26 may each be implemented in the CPU, in the GPU, or in a combination of the CPU and the GPU.

In the present embodiment, the various circuitries are each implemented in the CPU and/or GPU of processing apparatus 22 by means of a computer program having computer-readable instructions that are executable to perform the method of the embodiment. However, in other embodiments each circuitry may be implemented in software, hardware or any suitable combination of hardware and software. In some embodiments, the various circuitries may be implemented as one or more ASICs (application specific integrated circuits) or FPGAs (field programmable gate arrays).

In alternative embodiments the processing apparatus 22 comprising the projection circuitry 24 and rendering circuitry 26 may be part of any suitable medical diagnostic apparatus (for example a CT scanner or MR scanner) or image processing apparatus (for example, a PC or workstation). The processing apparatus 22 may be configured to process any appropriate modality of imaging data.

The processing apparatus 22 also includes a hard drive and other components including RAM, ROM, a data bus, an operating system including various device drivers, and hardware devices including a graphics card. Such components are not shown in FIG. 1 for clarity.

The apparatus of FIG. 1 is configured to perform a method as described below with reference to FIG. 2.

Figure 2:
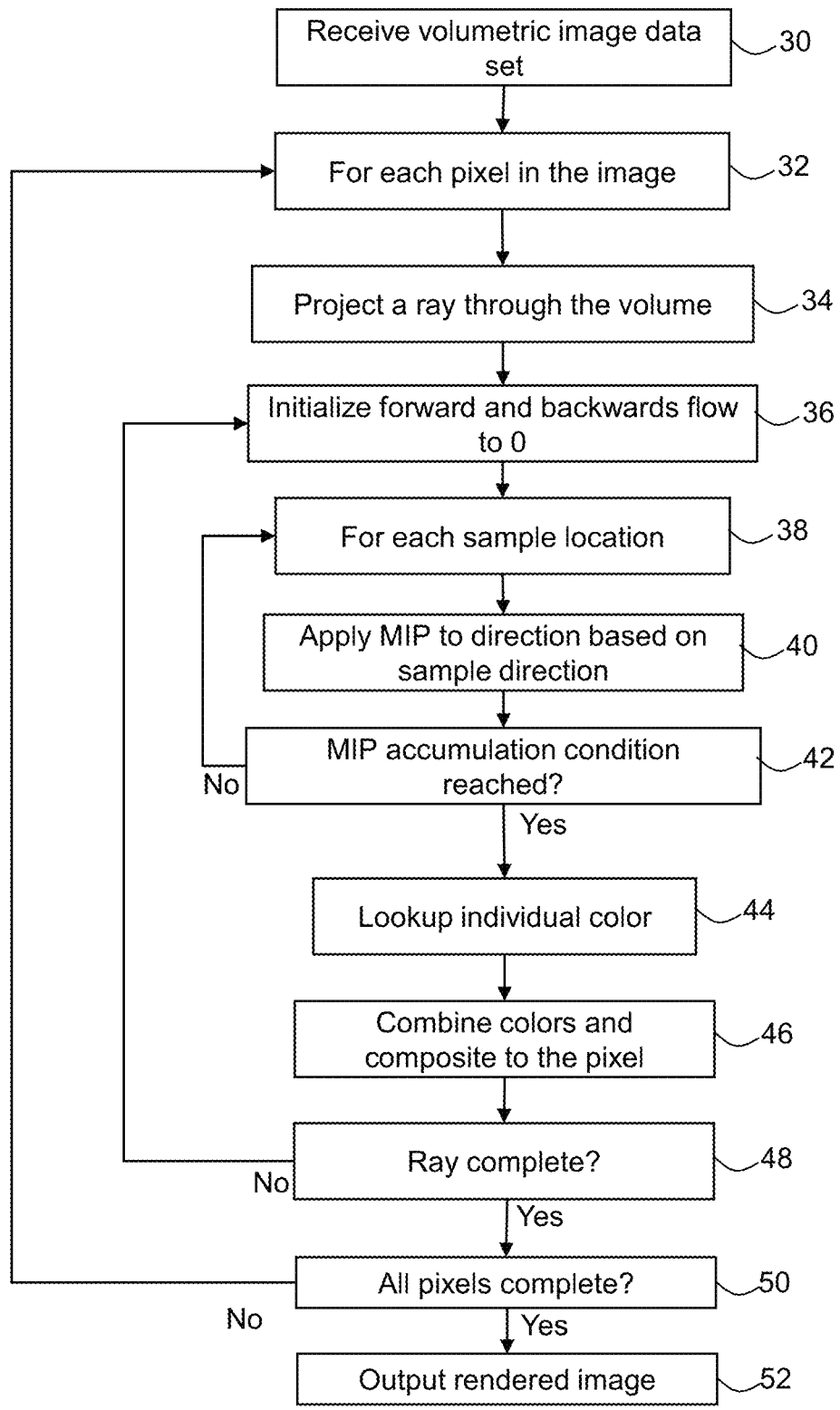
FIG. 2 is a flow chart illustrating in overview a method in accordance with an embodiment.

FIG. 2 is a flow chart illustrating in overview a method of rendering using a specific intensity projection mode for color Doppler imaging. In the embodiment of FIG. 2, the intensity projection mode is MIP. In other embodiments, other intensity projection modes may be used, for example minimum intensity projection or average intensity projection.

In summary, a velocity signal is separated into forward and backward flow. MIP values for forward and backward flow are accumulated separately. Accumulation is performed for regions in which a power value is greater than a power threshold value. When the accumulation ends, each direction is turned into an individual color by using two separate tables. The colors are then combined using a combining operator. In the case of vessels, ordering is achieved by executing the combining operator during the accumulation each time the power signal drops below the power threshold. To be more robust to noise, an exit condition may include a cumulative amount of power below the threshold value.

The method of FIG. 2 is now described in detail with reference to stages illustrated in FIG. 2. At stage 30, the projection circuitry 24 receives a volumetric data set. The volumetric data set is a set of three-dimensional image data that has been obtained by scanning a region of a patient using the measurement probe 14. A method of acquiring color ultrasound Doppler image data is described in Oglat A A, Matjafri M Z, Suardi N, Oqlat M A, Abdelrahman M A, Oqlat A A. A Review of Medical Doppler Ultrasonography of Blood Flow in General and Especially in Common Carotid Artery. J Med Ultrasound. 2018; 26(1):3-13. doi: 10.4103/JMU.JMU_11_17, which is hereby incorporated by reference.

The volumetric data set is representative of a three-dimensional array of voxels, each voxel representative of a particular position in three-dimensional space and each voxel having associated data values. In the present embodiment, the data values for each voxel comprise blood flow data comprising at least a power value and a velocity value for the voxel. The power value is a value for a power (or strength) component of an ultrasound Doppler imaging signal for the voxel, and is representative of a power or strength of the Doppler signal for the voxel. The velocity value is a value for a velocity component of an ultrasound Doppler imaging signal for the voxel, and is representative of a flow velocity for the voxel relative to an acquisition direction.

The projection circuitry 24 receives or defines a viewing direction from which an image is to be rendered. The projection circuitry 24 receives or defines positions of a plurality of pixels in the image to be rendered.

At stage 32, the projection circuitry 24 selects one of the pixels in the image to be rendered. The selection of pixels may be such that pixels are grouped to maintain resource usage coherence. In other embodiments, any suitable order of selection of pixels may be used. The method then proceeds to stage 34.

At stage 34, the projection circuitry 24 initiates projection of a ray through the volume of the volumetric data set from a position of the selected pixel, along the viewing direction.

At stage 36, before sampling values along the ray, the projection circuitry 24 initializes a forward flow value to zero and initializes a backward flow value to zero.

The projection circuitry 24 then starts to step through sample positions on the ray.

At stage 38, the projection circuitry 24 selects a sample position in the volume along the ray. In the present embodiment, the projection circuitry 24 steps along the ray using regular steps of a predetermined step size. In other embodiments, any suitable method of determining sample positions may be used.

In a first instance of stage 38, the sample position is the first sample position to be encountered when projecting the ray through the volume.

At stage 40, the projection circuitry 24 determines a velocity value at the selected sample position by interpolating velocity values for voxels neighboring the selected sample position. The interpolating of the velocity values may comprise, for example, linear interpolation or cubic interpolation. In some embodiments, only velocity values having the same sign are interpolated together. For example, if most of the neighboring voxels have positive velocity values, then neighboring voxels having negative velocity values may be excluded from the interpolation, or vice versa. Values for excluded voxels may be set to zero and values for included voxels may be boosted or normalized. In other embodiments, all velocity values are used in the interpolation, which may mean that negative velocity values cancel positive velocity values.

The projection circuitry 24 uses the determined velocity value for the voxel to determine whether the direction of flow at the selected sample position is forward or backward, for example forward or backward relative to direction of acquisition or forward or backward relative to a vessel in which the selected sample position lies. For example, the projection circuitry 24 may use a method as described in Oglat A A, Matjafri M Z, Suardi N, Oqlat M A, Abdelrahman M A, Oqlat A A. A Review of Medical Doppler Ultrasonography of Blood Flow in General and Especially in Common Carotid Artery. J Med Ultrasound. 2018; 26(1):3-13. doi: 10.4103/JMU.JMU_11_17.

It may be considered that positions at which the direction of flow is forward form part of a first region of flow, and positions at which the direction of flow is backward form part of a second, different region of flow.

The projection circuitry 24 determines a power value at the selected sample position by interpolating power values for voxels neighboring the selected sample position. The projection circuitry 24 determines whether the power value is greater than a predetermined power threshold value.

If the power value for the selected sample position is not greater than the power threshold value, nothing is added to either the forward flow value or the backward flow value.

If the power value for the selected sample position is greater than the power threshold value and the direction of flow is forward, the projection circuitry 24 applies a maximum intensity projection for the forward direction by setting the forward flow value to equal the velocity value for the selected sample position.

If the power value for the selected sample position is greater than the power threshold value and the direction of flow is backward, the projection circuitry 24 applies a maximum intensity projection for the backward direction by setting the backward flow value to equal the velocity value for the selected sample position.

At stage 42, the projection circuitry 24 determines whether a MIP accumulation condition has been reached. In other embodiments, the projection circuitry 24 may determine whether any suitable accumulation condition has been met. The accumulation condition may not be a MIP accumulation condition, for example in embodiments in which a different intensity projection is used.

In the embodiment of FIG. 2, a MIP accumulation condition is met if a power value drops below a threshold value such as the predetermined power threshold value. Power dropping below a threshold value may indicate a boundary of a vessel or other anatomical structure. Additionally, a MIP accumulation condition is met if a ray traversal through the volume ends.

In other embodiments, an accumulation condition may include the presence of a cumulative amount of power below the power threshold value, which may be obtained over more than one sample. In some embodiments, in order for an accumulation condition to be reached, a predetermined number of sampling points may be required to be below the power threshold value. For example, the accumulation condition may be met when two consecutive sampling points are below the power threshold value, or when three consecutive sampling points are below the power threshold value. In some embodiments, a MIP accumulation condition is met if a direction of flow changes.

If no MIP accumulation condition is reached, the process of FIG. 2 returns to stage 38, at which the projection circuitry 24 selects a sample position in the volume along the ray. At stage 40, the projection circuitry 24 determines a velocity value and a power value at the selected sample position. The projection circuitry 24 determines whether the power value is greater than a predetermined power threshold value. If the power value for the selected sample position is not greater than the power threshold value, nothing is added to either the forward flow value or the backward flow value.

If the power value for the selected sample position is greater than the power threshold value and the direction of flow is forward, the projection circuitry 24 applies a maximum intensity projection for the forward direction. If the velocity value for the selected sample position is not higher than the current forward flow value, no change is made to the forward flow value. If the velocity value for the selected sample position is higher than the current forward flow value, the current forward flow value is replaced with the power value for the selected sample position.

If the power value for the selected sample position is greater than the power threshold value and the direction of flow is backward, the projection circuitry 24 applies a maximum intensity projection for the backward direction. If the velocity value for the selected sample position is not higher than the current backward flow value, no change is made to the backward flow value. If the velocity value for the selected sample position is higher than the current backward flow value, the current backward flow value is replaced with the velocity value for the selected sample position.

Maximum intensity projection is thereby applied separately to sample positions having forward flow and sample positions having backward flow.

At stage 42, the projection circuitry 24 determines whether a MIP accumulation condition has been reached. If no MIP accumulation condition is reached, the process of FIG. 2 returns to stage 38.

If an accumulation condition is reached at stage 42, the process of FIG. 2 proceeds to stage 44. At stage 44, the rendering circuitry 26 looks up an individual color for the forward MIP accumulation represented by the forward flow value and looks up an individual color for the backward MIP accumulation represented by the backward MIP value.

Two separate color lookup tables are used. A first color lookup table, which may also be called a forward lookup table, comprises values for color corresponding to forward flow values. A second, different color lookup table, which may also be called a backward lookup table, comprises values for color corresponding to backward flow values. Each color value may comprise values for multiple color components, for example red, green and blue color components, and a value for opacity.

In the present embodiment, forward flow values are mapped to various shades of red by the forward lookup table, and backward flow values are mapped to various shades of blue by the backward lookup table. Forward and backward flow may therefore be distinguished by color.

The rendering circuitry 26 looks up the forward lookup table to find a color value corresponding to the current forward flow value, which may be referred to as a forward color value. The forward color value is dependent on the forward flow value. For example, a higher forward flow value may result in a greater intensity of color than a lower forward flow value. A higher forward flow value may result in a higher opacity than a lower forward flow value.

The rendering circuitry 26 looks up the backward lookup table to find a color value corresponding to the current backward flow value, which may be referred to as a backward color value. The backward color value is dependent on the backward flow value. For example, a higher backward flow value may result in a greater intensity than a lower backward flow value, and/or a higher backward flow value may result in a higher opacity than a lower backward flow value.

In other embodiments, color values may be obtained from any suitable color mapping resource or resources, for example any suitable list(s), table(s) or function(s). Any suitable method may be used to obtain color values for forward and backward MIP accumulations. In some embodiments, color values may be obtained by blending a plurality of predefined color values, for example two colors for each direction and one color in the middle near zero.

At stage 46, the rendering circuitry 26 combines colors and composites to the pixel. Stage 46 comprises two sub-stages. In a first sub-stage, the rendering circuitry 26 uses a combining operator to combine the forward color value for the current accumulation and the backward color value for the current accumulation to obtain a combined color value. Different embodiments may use different combining operators to perform the first sub-stage of stage 46, as described below. In a second sub-stage, the rendering circuitry 26 composites the combined color value with any color value that has previously been written to the pixel as a result of any previous accumulations.

In the embodiment of FIG. 2, the combining operator is based on a compositing method. The forward flow color is over the backward flow color. Relative to a viewer, the color that represents the forward flow value appears to be in front of the color that represents the backward flow value that is accumulated for the same part of the ray. The relationship between the forward direction and the backward direction is static. The opacity for the forward direction determines how much the color for the backward direction shows behind the color for the forward direction.

In other embodiments, the combining operator is such that the color representing the backward direction is over the color representing the forward direction. The combining may be biased so that one of the direction is always on top of the other direction.

In further embodiments, the combining operator is such that a fastest flow is on top. A global maximum of the forward flow value and backward flow value is performed to find the fastest flow, which may be either forward or backward. The combining of the colors is then biased to put the direction with the fastest flow on top. Such embodiments may be considered to provide a hybrid of global MIP and a two-direction approach.

In further embodiments, the combining operator is such that a highest power is on top. A maximum velocity may be accumulated but a highest power may be chosen when a direction is swapped.

In further embodiments, the combining operator determines a main component. A main component is the direction that had the most valid samples during the accumulation. The projection circuitry 24 counts a number of samples contributing to the forward direction and a number of samples contributing to the backward direction. When the accumulation condition is reached, the projection circuitry 24 selects the direction having the most samples as a main component. The main component may be considered to be the direction that is most dominant. The combining operator combines the colors for the forward and backward directions such that the main component is on top.

In other embodiments, a clamped forward and backward color are used. Colors are added together when a transition point is reached, which may be when an accumulation condition is reached. Flow from one direction looks normal. An intersection of both directions may look oversaturated, for example white.

In other embodiments, a power modulated combining operator is used. For example, a combined color may equal max forward power*forward color+max backward power*backward color/(max forward power+max backward power). This is an additive approach but color is based on flow parameters, such that the stronger signal is preferred over the weaker signal. In this example, the color is normalized. In other embodiments any suitable modulation of the color may be used.

An output of the first sub-stage of stage 46 is a combined color that has been obtained by combining colors that are representative of forward and backward flow for a current accumulation.

At the second sub-stage of stage 46, the combined color is composited with any color that has previously been written to the pixel, and a color resulting from the compositing is written to the pixel. In a first instance of stage 46, no previous color has been added to the pixel and so the compositing may be omitted.

At stage 48, the projection circuitry 24 determines whether the ray has passed through the entire volume. If the ray has not yet passed through the entire volume, the process of FIG. 2 returns to stage 36 to perform a further accumulation. The projection circuitry 24 resets the forward flow value and the backward flow value to zero. New MIP accumulations of forward and backward flow are performed until a MIP accumulation condition is reached.

When the MIP accumulation condition is reached, the rendering circuitry 26 looks up individual colors in the forward lookup table and in the backward lookup table. At the first sub-stage of stage 46, the rendering circuitry 26 combines the color values for forward flow and backward flow using a combining operator as described above, to obtain a combined color value for the further accumulation.

At a second sub-stage of stage 46, the rendering circuitry 26 composites the combined color value for the further accumulation with the combined color value that was obtained for the first accumulation and written to the pixel in the first instance of stage 46. The composing may be performed using the color over or under operator where a portion of the color for the further accumulation is added based on the opacity obtained for the first accumulation. A resulting color value is written to the pixel.

In the compositing of the second sub-stage, a spatial ordering is maintained. The color obtained from the accumulation that is closer to the viewer appears on top of the color obtained from the accumulation that is further from the viewer. A result of the further compositing is written to the pixel.

It is noted that accumulation may be performed multiple times along the ray, with separate colors resulting from the separate accumulations. In each accumulation, forward and backward flow are accumulated separately and colors representative of forward and backward flow are combined using the combining operator to obtain a combined color. The combined color is then composited with any color value that has been written to the pixel as a result of one or more previous accumulations.

In the method of FIG. 2, colors from different accumulations are composited at the end of each accumulation. In other embodiments, colors from different accumulations may be composited only once the ray is complete.

Stages 36 to 46 are performed until the ray has passed through the entire volume. If at stage 48 the projection circuitry 24 determines that the ray has passed through the entire volume, the process of FIG. 2 proceeds to stage 50.

At stage 50, the projection circuitry 24 determines whether rays have been cast for all pixels. If not, the method of FIG. 2 returns to stage 32 and a further pixel is selected.

If rays have been cast for all pixels, and colors determined for all pixels, the method of FIG. 2 proceeds to stage 52. At stage 52, the rendering circuitry 26 outputs a rendered image comprising the colors determined for each pixel. For example, the rendered image may be displayed on main display screen 16.

The method of FIG. 2 provides a MIP based visualization mode that may be used with three-dimensional or four-dimensional ultrasound color Doppler. The interior of a region of flow, for example in a vessel, is visualized with a modified MIP algorithm. The modified MIP highlights interior flow, which can be difficult to visualize using other types of volume rendering, for example shaded direct volume rendering.

The algorithm of FIG. 2 divides a velocity signal into specific forward and backward directions and accumulates two MIP values, one for each direction. When the MIP accumulation ends, results from the accumulation of forward flow and the accumulation of backward flow are turned into colors and combined. The same accumulation of forward flow, accumulation of backward flow, and combining is also provided for any subsequent accumulation. Results for different accumulations are then composited in order.

In the case of vessels, the method of FIG. 2 achieves ordering by executing the combining operator during accumulation every time the power signal drops below the power threshold. When the ray finishes passing through a vessel, an accumulation is completed and the rendering circuitry 26 looks up forward and backward colors, which are combined using the combining operator. Colors obtained for different vessels are then composited in order.

Figure 3A:
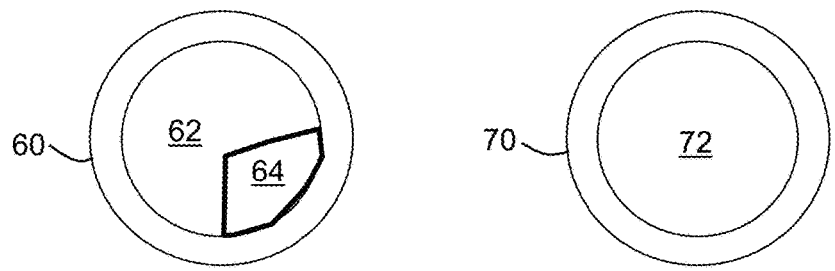
FIG. 3A is a schematic illustration of two vessels in cross section.

FIGS. 3A, 3B, 3C and 3D illustrate a simple example of use of the method of FIG. 2. FIG. 3A is a schematic illustration showing cross-sections of two vessels 60, 70 which are present in a volume. A first vessel 60 comprises a forward flow region 62 and a backward flow region 64. A second vessel 70 comprises only a backward flow region 72.

Figure 3B:
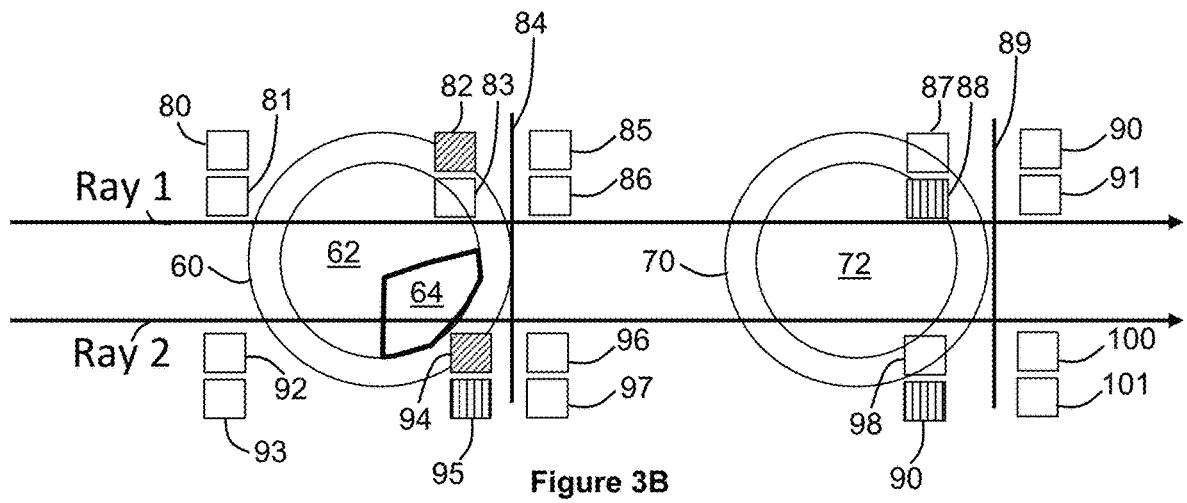
FIG. 3B is a schematic illustration of a first ray and second ray projected through the two vessels of FIG. 3A.

FIG. 3B shows two rays passing through the first vessel 60 and second vessel 70. The two rays obtain pixel colors using accumulation with a blue over red combining operator, and a two level composition condition.

A first ray, Ray 1, performs the method of FIG. 2 to accumulate values and translate the values to colors. At a first position on Ray 1 which is before the first vessel 60, no color is accumulated in the forward direction as represented in box 80 by an empty box, and no color is accumulated in the backward direction as represented in box 81 by an empty box.

At a second position on Ray 1 which is most of the way through the first vessel 60, color has been accumulated in the forward direction as represented by box 82 which is filled. A first shading is used in box 82 to represent a red color which is obtained from looking up a forward flow value obtained by accumulating through the first vessel. No color has been accumulated in the backward direction as represented in box 83 which is empty.

A line 84 at the end of first vessel 60 indicates a position at which an accumulation condition is met. When the accumulation condition is met, the forward flow color represented in box 82 and the backward flow color represented in box 83 are combined by the rendering circuitry 26 and composited to the pixel of Ray 1. In the example of FIG. 3, there is no color in box 83 so the combined color is the red color of box 82.

At a third position on Ray 1 which is just after the accumulation condition has been met, the forward flow value has been reset to zero as represented by empty box 85, and the backward flow value has been reset to zero as represented by empty box 86.

At a fourth position on Ray 1 which is most of the way through the second vessel 70, no color has been accumulated in the forward direction as represented by box 87 which is empty. Color has been accumulated in the backward direction as represented by box 88.

A second shading is used in box 88 to represent a blue color which is obtained from looking up a backward flow value obtained by accumulating through the second vessel.

A line 89 at the end of second vessel 70 indicates a position at which an accumulation condition is met. The accumulation through the second vessel 70 is separate from the accumulation through the first vessel 60. When the accumulation condition is met for the accumulation through the second vessel, the rendering circuitry 26 combines the forward flow color represented in box 87 and the backward flow color represented in box 88. In the example of FIG. 3, there is no color in box 87 so the combined color is the blue color of box 88. The rendering circuitry 26 composites the combined color obtained from the second accumulation through the second vessel 70 with the combined color obtained from the first accumulation through the first vessel 60 and writes the resulting color to the pixel.

At a fifth position on Ray 1 which is just after the accumulation condition has been met after the second vessel, the forward flow value has been reset to zero as represented by empty box 90, and the backward flow value has been reset to zero as represented by empty box 91.

A second ray, Ray 2, performs the method of FIG. 2 to accumulate values and translate the values to colors. Ray 2 passes through different parts of vessels 60, 70 than those passed through by Ray 1. Accumulation for Ray 2 is shown at first, second, third, fourth and fifth positions corresponding to the positions described above in relation to Ray 1.

At the first position on Ray 2 which is before the first vessel 60, no color is yet accumulated in the forward direction as represented in box 92 by an empty box, and no color is yet accumulated in the backward direction as represented in box 93 by an empty box.

At the second position on Ray 2 which is most of the way through the first vessel 60, color has been accumulated in both the forward direction as represented by box 94 and the backward direction as represented by box 95. This is because Ray 2 passes through both the forward flow region 62 and the backward flow region 64 of first vessel 60. A first shading is used in box 94 to represent a red color obtained by looking up a lookup table for forward flow and a second shading is used in box 95 to represent a blue color obtained by looking up a lookup table for backward flow.

Line 84 at the end of first vessel 60 indicates a position at which an accumulation condition is met. When the accumulation condition is met, the forward flow color represented in box 94 and the backward flow color represented in box 95 are combined by the rendering circuitry 26 and composited to the pixel of Ray 2.

At the third position which is after the accumulation condition has been met, the forward flow value is reset to zero as represented by empty box 96, and the backward flow value is reset to zero as represented by empty box 97.

At a fourth position on Ray 2 which is most of the way through the second vessel 70, no color has been accumulated in the forward direction as represented by box 98 which is empty. Color has been accumulated in the backward direction as represented by box 99. A second shading is used in box 99 to represent a blue color which is obtained from looking up a backward flow value obtained by accumulating through the second vessel.

Line 89 at the end of second vessel 70 indicates a position at which an accumulation condition is met. When the accumulation condition through the second vessel 70 is met, the forward flow color represented in box 98 (which in this example is empty) and the backward flow color represented in box 99 are combined by the rendering circuitry 26 and are then composited with the result of the first accumulation through the first vessel A result is written to the pixel of Ray 2.

At a fifth position on Ray 2 which is just after the accumulation condition has been met after the second vessel, the forward flow value has been reset to zero as represented by empty box 100, and the backward flow value has been reset to zero as represented by empty box 101.

Figure 3C:
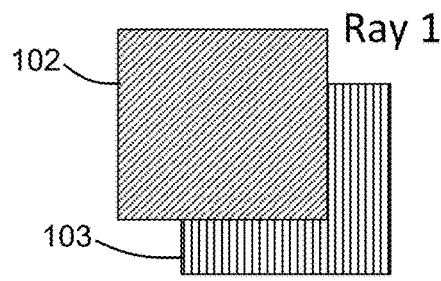
FIG. 3C is a schematic illustration of the results of two accumulations along the first ray.

FIG. 3C represents the composition performed for Ray 1 along with other rays in a small square region including Ray 1. The composition performed for Ray 1 composites color obtained in the first accumulation through the first vessel 60 with color obtained in the second accumulation through the second vessel 70. The composition may be performed using a color over or under operator, which maintains spatial order. Similar compositions are performed for other rays in the small square region including Ray 1.

A first color obtained by accumulation through the first vessel 60 is represented in box 102. The shading of box 102 represents a red color. A second color obtained by accumulation through the second vessel 70 is represented in box 103. The shading of box 103 represents a blue color. As the colors represent different power regions, the red and the blue are spatially ordered. Box 102 which is representative of the first vessel 60 is on top of box 103 which is representative of the second vessel 70. If there is variation of power through the vessel, what will be seen is a red that is representative of the maximum intensity in first vessel 60 on top of a blue that is representative of the maximum intensity in second vessel 70.

Figure 3D:
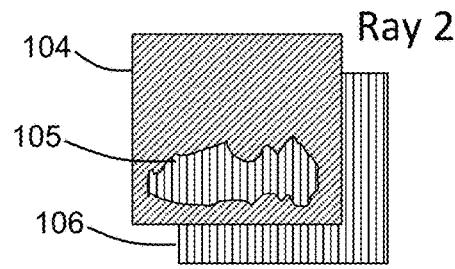
FIG. 3D is a schematic illustration of the results of two accumulations along the second ray.

FIG. 3D represents the composition performed for Ray 2 along with other rays in a further small square region including Ray 2. The composition performed for Ray 2 composites color obtained in the first accumulation through the first vessel 60 with color obtained in the second accumulation through the second vessel 70. The composition may be performed using a color over or under operator, which maintains spatial order.

In the case of Ray 2, Ray 2 passes through both forward region 62 and backward region 64 of first vessel 60, so both forward and backward values are accumulated. At the end of the first accumulation, red representative of the forward region is composited with blue representative of the backward region. Box 104 represents color from the first accumulation of Ray 2 through the first vessel 60 along with color obtained from similar accumulations from other rays in the further small square region. Box 104 mostly comprises shading representing a red color, but with a region of shading 105 that represents a blue color and is overlaid on top. Color within the first accumulation is biased such that backward flow is shown over forward flow. Box 106 represents color from the second accumulation 70 of Ray 2 along with color obtained from similar accumulations from other rays in the further small square region. Box 106 comprises shading representing a blue color. The accumulations from the different vessels are still kept separate and ordering between the different vessels is maintained.

The method of FIG. 2 may be used to render various examples of ultrasound color Doppler images.

In one example, the method of FIG. 2 is used to render two vessels. Shaded direct volume rendering is also used to render the two vessels for comparison, using a ray-casting algorithm. In an image rendered using shaded direct volume rendering, what is shown may be mostly the outer part of the vessels, in which the flow is slow. Only hints of the inner flow may be seen, for example at a cut across a vessel. Alternatively, the rendered image may provide a very blurred exterior.

When using the method of FIG. 2, the inner flow in the vessels is more visible. A viewer can see the inner flow which is faster than flow at the exterior of the vessel. Furthermore, the viewer can see direction of flow as represented by color. Ordering of vessels as provided by how accumulations for the vessels are composited, which maintains spatial ordering.

Figure 4A:
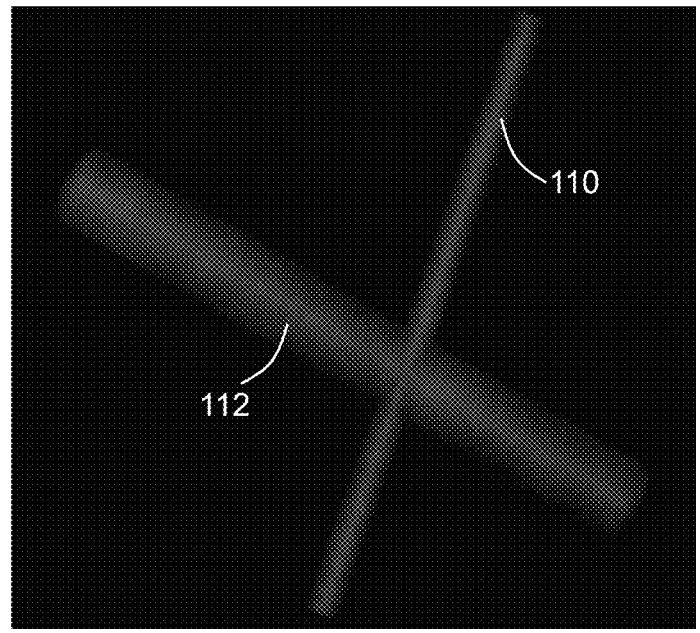
FIG. 4A is an example of an image rendered using a method in accordance with an embodiment.

FIG. 4A shows an image rendered using the method of FIG. 2. Two vessels 110, 112 are present in a volume. FIG. 4A is shown in greyscale. However, in practice, FIG. 4A would be rendered such that vessel 110 is shown in blue and vessel 112 is shown in red. A user viewing the rendered image can distinguish the vessel by color, and is shown regions of fastest flow due to the MIP accumulations of forward and backward flow.

Figure 4B:
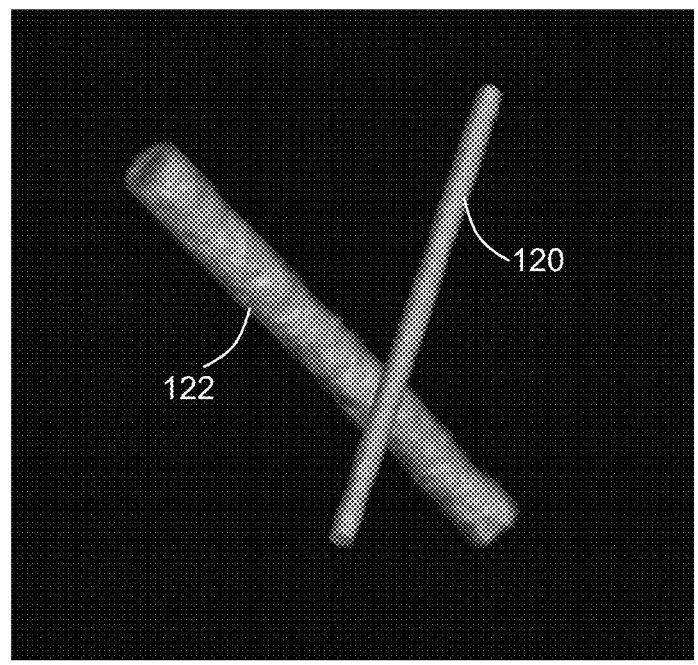
FIG. 4B is an example of an image rendered using shaded direct volume rendering.

FIG. 4B shows an image rendered using a shaded direct volume rendering method. Two vessels 120, 122 are present in a volume. FIG. 4B is shown in greyscale. However, in practice, FIG. 4B could be rendered such that vessel 120 is shown in blue and vessel 122 is shown in red. If such a rendering were performed, a user viewing the rendered image would see mostly the boundary of each vessel, and would have very little view of the inside of the vessel. The vessels would appear pale because the flow at the boundary of the vessel is low compared with flow inside the vessel.

In a further example (not illustrated), a dataset that is representative of an umbilical cord is rendered using the method of FIG. 2, and is also rendered using shaded direct volume rendering, for example as a B mode volume. In the image rendered using shaded direct volume rendering, lighter areas which are representative of slower flow are dominant. A better representation of flow may be obtained using the method of FIG. 2, in which separate maximum intensity accumulations allow for separate projections of the forward flow and backward flow. Areas of forward flow and backward flow are represented in different colors, for example red and blue, and are ordered.

In some embodiments, an image rendered using the method of FIG. 2 is combined or overlaid with an image rendered using a different rendering method, for example a B mode volume. The images may be overlaid. Alternatively, the different rendering method may be performed within each accumulation.

Embodiments described above comprise rendering of ultrasound color Doppler data that is representative of blood flow. In other embodiments, any suitable medical imaging data that is representative of flow may be used. The medical imaging data may be obtained by scanning at least part of a human or animal subject using any suitable modality. For example, the medical imaging data may be obtained using MRI FBI (Fresh Blood Imaging) or FFR-CT (fractional flow reserve CT).

In some embodiments, MRI FBI tracks movement by applying spin rotation pulse to a region of interest comprising tissue and blood. By the time that the spin decays back into the direction of a B field of the MRI FBI, the blood has moved in position and a corresponding signal has also moved. Three-dimensional flow data is obtained using MRI FBI and rendering of the three-dimensional flow data is performed using intensity projection as described above.

In some embodiments, FFR-CT tracks contrast progression and movement and/or shape, and uses simulation to get an flow estimate. Three-dimensional flow data is obtained using FFR-CT and rendering of the three-dimensional flow data is performed using intensity projection as described above.

The medical imaging data may be representative of flow of any appropriate fluid that moves within the body. In some embodiments, the fluid is urine, for example in the bladder. In some embodiments, the fluid is cerebrospinal fluid (CSF), for example intracranial CSF.

In further embodiments, rendering may be performed of any suitable flow data, which may not be medical.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical imaging apparatus, comprising:
processing circuitry configured to:
receive three-dimensional flow data, wherein the three-dimensional flow data comprises data acquired by medical imaging of a subject;
perform a first intensity projection to process first flow data corresponding to a first region in the three-dimensional flow data having a first, forward direction of flow in a vessel, thereby obtaining a first color;
perform a second, independent intensity projection to process second flow data corresponding to a second region in the three-dimensional flow data having a second, backward direction of flow in the vessel thereby obtaining a second color;
and
generate volume rendering image data to obtain an image for a viewing direction, which includes combining the first color and the second color to obtain a combined color, wherein the first and second intensity projections each pass through at least part of both the first and second regions along the viewing direction, and the combined color is used for at least one pixel of the image thereby to represent, by the at least one pixel using the combined color, both the flow in the first, forward direction and the flow in the second, backward direction.

2. The apparatus according to claim 1, wherein the medical imaging comprises ultrasound Doppler imaging.

3. The apparatus according to claim 1, wherein the medical imaging comprises MRI FBI (Fresh Blood Imaging) or FFR-CT (fractional flow reserve CT) imaging.

4. The apparatus according to claim 1, wherein the three-dimensional flow data received by the processing circuitry comprises three-dimensional blood flow data.

5. The apparatus according to claim 1, wherein the three-dimensional flow data received by the processing circuitry is representative of a flow of urine or cerebrospinal fluid.

6. The apparatus according to claim 1, wherein the three-dimensional flow data received by the processing circuitry comprises at least a respective power value and a respective velocity value for each of a plurality of voxels of the three-dimensional flow data.

7. The apparatus according to claim 6, wherein the processing circuitry is further configured to determine whether the plurality of voxels of the three-dimensional flow data are part of the first region or the second region based on the velocity values.

8. The apparatus according to claim 6, wherein the processing circuitry is further configured to apply a power threshold to the plurality of voxels of the three-dimensional flow data such that the first intensity projection and second intensity projection process voxels having a power value above the power threshold.

9. The apparatus according to claim 1, wherein the processing circuitry is further configured to:
   perform the first intensity by accumulating velocity values for the first region over at least part of a ray that traverses a volume of the three-dimensional flow data;
   perform the second intensity projection by accumulating velocity values for the second region over the at least part of the ray; and
   perform the accumulating of the velocity values for the first and the second region until an accumulation condition is reached.

10. The apparatus according to claim 9, wherein the accumulation condition comprises at least one of
   the ray exiting the volume;
   a predetermined number of samples falling below a power threshold; or
   an accumulation of difference in power values falling under a cumulative power threshold.

11. The apparatus according to claim 9, wherein the processing circuitry is further configured to
   perform additional first and second intensity projections along a further part of the ray to obtain additional first and second colors;
   combine the additional first and second colors to obtain an additional combined color; and
   composite the combined color and the additional combined color.

12. The apparatus according to claim 11, wherein the processing circuitry is further configured to composite the combined color and the additional combined color to maintain an order along the ray.

13. The apparatus according to claim 1, wherein the processing circuitry is further configured to obtain the first color by obtaining the first color from a first color mapping resource, and obtain the second color by obtaining the second color from a second, different color mapping resource.

14. The apparatus according to claim 13, wherein the first color mapping resource comprises a first lookup table and the second color mapping resource comprises a second, different lookup table.

15. The apparatus according to claim 1, wherein the processing circuitry is further configured to combine the first color and the second color using a combining operator.

16. The apparatus according to claim 15, wherein the processing circuitry is further configured to combine the first color and the second color using the combining operator, which combines the first color and second color such that the first color for the forward direction is over the second color for the backward direction, or combines the first color and second color such that the second color for the backward direction is over the first color for the forward direction.

17. The apparatus according to claim 16, wherein at least one of the processing circuitry is further configured to determine which of the first flow data and the second flow data has a faster flow, and the combining operator combines the first color and second color such that the one of the first color and second color that corresponds to the flow data having the faster flow is over the other of the first color and the second color;
   the processing circuitry is further configured to determine which of the first flow data and the second flow data has a higher power, and the combining operator combines the first color and second color such that the one of the first color and second color that corresponds to the flow data having the higher power is over the other of the first color and the second color;
   the processing circuitry is further configured to determine which of the first flow data and the second flow data has a highest number of samples over a power threshold, and the combining operator combines the first color and second color such that the one of the first color and second color that corresponds to the flow data having the highest number of samples over said power threshold is over the other of the first color and the second color;
   the combining operator adds the first color and the second color; or
   the processing circuitry is further configured to determine a maximum power of the first flow data and determines a maximum power of the second flow data, and the combining operator modulates the first color using the maximum power of the first flow data, modulates the second color using the maximum power of the second flow data, and adds the modulated first color and the modulated second color.

18. The apparatus according to claim 1, wherein the processing circuitry is further configured to perform a further volume rendering of the three-dimensional flow data to obtain further volume rendering image data, and combine or overlay the volume rendering image data with the further volume rendering image data.

19. A medical imaging method, comprising:
   receiving three-dimensional flow data, wherein the three-dimensional blood flow data comprises data acquired by medical imaging of a subject;
   performing a first intensity projection to process first flow data corresponding to a first region in the three-dimensional flow data having a first, forward direction of flow in a vessel, thereby obtaining a first color;

performing a second, independent intensity projection to process second flow data corresponding to a second region in the three-dimensional flow data having a second, backward direction of flow in the vessel thereby obtaining a second color; and generating volume rendering image data to obtain an image for a viewing direction, which includes combining the first color and the second color to obtain a combined color, wherein the first and second intensity projections each pass through at least part of both the first and second regions along the viewing direction, and the combined color is used for at least one pixel of the image thereby to represent, by the at least one pixel using the combined color, both the flow in the first, forward direction and the flow in the second, backward direction.

20. A medical imaging apparatus, comprising:
processing circuitry configured to:
receive three-dimensional flow data, wherein the three-dimensional flow data comprises data acquired by medical imaging of a subject;
perform a first intensity projection to accumulate values for a first region over at least a portion of a ray traversing a volume of the three-dimensional flow data, thereby obtaining a first color, the first region having a first, forward direction of flow;
perform a second, independent intensity projection to accumulate values for a second region over at least a portion of the ray traversing the volume of the three-dimensional flow data, thereby obtaining a second color, the second region having a second, backward direction of flow;
and
generate volume rendering image data to obtain an image for a viewing direction, which includes combining the first color and the second color to obtain a combined color, wherein the first and second intensity projections each pass through at least part of both the first and second regions along the viewing direction, and the combined color is used for at least one pixel of the image thereby to represent, by the at least one pixel using the combined color, both the flow in the first, forward direction and the flow in the second, backward direction.

* * * * *